(12) United States Patent
Koppel

(10) Patent No.: US 7,998,991 B2
(45) Date of Patent: *Aug. 16, 2011

(54) NEUROTHERAPEUTIC TREATMENT FOR SEXUAL DYSFUNCTION

(75) Inventor: Gary A. Koppel, Indianapolis, IN (US)

(73) Assignee: Revaax Pharmaceuticals, LLC, Indianapolis, IN (US)

( * ) Notice: Subject to any disclaimer, the term of this patent is extended or adjusted under 35 U.S.C. 154(b) by 1053 days.

This patent is subject to a terminal disclaimer.

(21) Appl. No.: 11/562,311

(22) Filed: Nov. 21, 2006

(65) Prior Publication Data

US 2007/0093466 A1    Apr. 26, 2007

Related U.S. Application Data

(62) Division of application No. 10/175,092, filed on Jun. 18, 2002, now Pat. No. 7,166,626.

(60) Provisional application No. 60/299,060, filed on Jun. 18, 2001.

(51) Int. Cl.
*A61K 31/42* (2006.01)

(52) U.S. Cl. ..................................... 514/375

(58) Field of Classification Search .............. 514/375
See application file for complete search history.

(56) References Cited

U.S. PATENT DOCUMENTS

| | | | |
|---|---|---|---|
| 4,127,118 | A | 11/1978 | Latorre |
| 5,256,652 | A | 10/1993 | El-Rashidy |
| 5,658,887 | A | 8/1997 | Gisby |
| 6,177,421 | B1 | 1/2001 | Moir |
| 6,426,342 | B2 | 7/2002 | Koppel |
| 6,610,681 | B1 | 8/2003 | Koppel |
| 6,627,625 | B1 | 9/2003 | Koppel |
| 7,166,626 | B2 | 1/2007 | Koppel |

OTHER PUBLICATIONS

Merck Manual of Diagnosis and Therapy, 16th ed., 1992, pp. 1573-1574.

*Primary Examiner* — San-Ming Hui
(74) *Attorney, Agent, or Firm* — Venable LLP; Keith G. Haddaway; Nancy J. Axelrod

(57) ABSTRACT

A method for improving sexual function is described. A mammal suffering from sexual dysfunction or otherwise in need of enhanced sexual function is administered a compound selected from those that are capable of inhibiting the activity of β-lactams, penicillin-binding proteins, and carboxypeptidases. Such compounds, including particularly β-lactam ring-containing compounds, can be used to formulate pharmaceutical formulations useful for improving sexual function.

29 Claims, 7 Drawing Sheets

NEUROTHERAPEUTIC TREATMENT FOR SEXUAL DYSFUNCTION

CROSS REFERENCE TO RELATED APPLICATION

This application is a divisional of U.S. Ser. No. 10/175,092, filed Jun. 18, 2002, now U.S. Patent No. 7,166,626, which claims priority to U.S. Provisional application No. 60/299,060, filed on Jun. 18, 2001.

FIELD OF THE INVENTION

This invention relates to a method for improving sexual function. More particularly, this invention is directed to the use of compounds capable of exhibiting specific binding affinity to and inhibiting the activity of certain bacterial enzymes and structurally related mammalian enzymes for improving sexual function and for reducing or eliminating the indicia of sexual dysfunction in a mammal either suffering from such disability or exposed to conditions tending to engender such disability.

BACKGROUND OF THE INVENTION

Sexual dysfunction is characterized by a disturbance in the processes that are involved in the sexual response cycle or by pain associated with sexual intercourse. The sexual response cycle comprises the four phases of desire, excitement, orgasm and resolution. Disorders of sexual response may occur at one or more of these phases. The sexual dysfunctions include sexual desire disorders, sexual arousal disorders, orgasmic disorders and sexual pain disorders. Sexual dysfunctions cause marked distress and-interpersonal difficulty. While progress has been made in the treatment of such disorders, there remains significant need for alternative therapeutic approaches.

A normal erection occurs as a result of a coordinated vascular event in the penis. This is usually triggered neurally and consists of vasodilation and smooth muscle relaxation in the penis and its supplying arterial vessels. Arterial inflow causes enlargement of the substance of the corpora cavemosa. Venous outflow is trapped by this enlargement, permitting sustained high blood pressures in the penis sufficient to cause rigidity. Muscles in the perineum also assist in creating and maintaining penile rigidity. Erection may be induced centrally in the nervous system by sexual thoughts or fantasy, and is usually reinforced locally by reflex mechanisms. Erectile mechanics are substantially similar in the female for the clitoris. Impotence or male erectile dysfunction is defined as the inability to achieve and sustain an erection sufficient for intercourse. Impotence in any given case can result from psychological disturbances (psychogenic), from physiological abnormalities in general (organic), from neurological disturbances (neurogenic), hormonal deficiencies (endocrine) or from a combination of the foregoing. These descriptions are not exact, however. There is currently no standardized method of diagnosis or treatment. As used herein, psychogenic impotence is defined as functional impotence with no apparent overwhelming organic basis. It may be characterized by an ability to have an erection in response to some stimuli (e.g., masturbation, spontaneous nocturnal, spontaneous early morning, video erotica, etc.) but not others (e.g., partner or spousal attention). Various methods for the treatment of impotence have been suggested, including external devices, for example, tourniquets (see U.S. Pat. No. 2,818,855). In addition, penile implants, such as hinged or solid rods and inflatable, spring driven or hydraulic models, have been used for some time. The administration of erection effecting and enhancing drugs is taught in U.S. Pat. No. 4,127,118 to LaTorre. That patent teaches a method of treating male impotence by injecting into the penis an appropriate vasodilator, in particular, an adrenergic blocking agent or a smooth muscle relaxant to effect and enhance an erection. More recently, U.S. Pat. No. 4,801,587 to Voss et al. teaches the application of an ointment to relieve impotence. The ointment consists of the vasodilators papaverine, hydralazine, sodium nitroprusside, phenoxybenzamine, or phentolamine and a carrier to assist absorption of the primary agent through the skin. U.S. Pat. No. 5,256,652 to El-Rashidy teaches the use of an aqueous topical composition of a vasodilator such as papaverine together with hydroxypropyl-.beta.-cyclodextrin. Sexual functions in females can be divided into several broad areas: desire, arousal, and orgasm. Studies have indicated that up to 63% of women exhibit dysfunctions in either arousal or orgasmic stages of sexual activities (Frank E, et al., 1978. N Engl J Med 299: 111). Sexual disorders such as dyspareunia and vaginismus, reduce the arousal phase of female sexual functioning. Impaired clitoral responsiveness can lead to orgasmic disorders. The prevalence of female sexual dysfunction increases with age (Goldstein M and Teng N. 1991, Clin Geriatr Med 7:41; Thirlaway K et al., 1996. Quality of Life Res 5:81; Slob A et al., 1990, J Sex Martial Ther 16:59). Vascular risk factors of coronary diseases also increase the probability of sexual dysfunction in postmenopausal females (Sadeghi-Nejad H et al., 1996, J Urol 155:677A). Female sexual dysfunction can be due to an impairment in endothelium dependent vasodilation and smooth muscle relaxation which in turn could lead to impairment of vascular dependent events associated with sexual functioning. During sexual arousal, an increase in vaginal blood flow occurs which in turn results in vaginal lengthening and enhanced production of vaginal fluid. Enhanced clitoral blood flow occurs during arousal leading to clitoral engorgement and erection. Impairment of these vascular dependent events can lead to impairment in vaginal lubrication and/or a diminution in vaginal enlargement during the arousal stage of female sexual function. An abnormality in these vascular dependent events could impair the arousal and/or orgasmic phases of sexual functioning.

SUMMARY OF THE INVENTION

The present invention provides a unique therapeutic approach to improving sexual function or the treatment of sexual dysfunction by what is presently believed to be a mechanism comprising inhibition of one or more neurogenic peptidases and a consequent therapeutically beneficial change in the concentrations of multiple neurologically significant neurotransmitters in the brain.

The method comprises the step of administering to a mammal suffering from or disposed to develop sexual dysfunction, or otherwise in need of enhanced sexual function, a compound which exhibits specific binding affinity to, and which inhibits function, of an enzyme selected from a group consisting of β-lactamase, penicillin-binding protein, and carboxy-peptidase in an amount effective to promote normal or enhanced sexual function of said mammal. The compound should possess sufficient blood-brain barrier transport properties so that blood levels of said compound achieved by any one of a wide variety of routes of administration, can provide a concentration of said compound in the central nervous system of the mammal undergoing treatment effective to improve sexual function, either by inhibiting the activity of one or more neurogenic enzymes, for example, carboxy peptidases and/or by another yet undefined mechanism of action. Treatment is effective in males, evidenced by enhanced erectile function, and in females evidenced, for example, by enhanced solicitation behavior.

In one embodiment of the invention the compound is a β-lactam ring-containing compound which is capable of inhibiting the biological activity of a β-lactamase, a penicillin-binding protein, or a carboxy peptidase such as carboxy peptidase E. In one embodiment the compound is clavulanic acid or a pharmaceutically acceptable salt or ester thereof. Other compounds recognized for their β-lactamase activity, their antibiotic activity, and/or their ability to inhibit carboxypeptidase E or other neurologically significant carboxy peptidases and having the requisite threshold blood-brain barrier transport property can be employed beneficially in accordance with the present method. Such compounds can be administered by any one of a wide variety of art-recognized routes of administration, including but not limited to oral ingestion, or parenteral, transdermal, inhalation, sublingual or buccal administration. Dosage ranges depend on the patient condition/circumstances and the pharmacologically significant properties of the therapeutic compound including, for example, minimum inhibitory concentration, absorption, protein binding, blood-brain barrier transport and the like, and dosage levels can be determined by extrapolation of effective concentrations in test animals. Typically the compounds are administered in accordance with this invention one to four times a day at a dose of about 0.01 to about 10 mg/kg, about 0.1 to about 10 mg/kg, or up to about 0.2 mg/kg to about 10 mg/kg. Unit dosage forms can be prepared to contain about 1 mg to about 500 mgs of the β-lactam compound in combination with a pharmaceutically acceptable carrier determined typically by the targeted route of administration. Optionally the β-lactam compound can be formulated in a prolonged release dosage form from which effective amounts of the compound are released over a period of about three hours to about one week or more. Methods for preparing such controlled release dosage forms are well known in the art and can be applied to formulate the compounds for use in accordance with this invention.

BRIEF DESCRIPTION OF THE DRAWINGS

FIG. 4B is similar to FIG. 4A except that it graphically depicts the relative concentration of serotonin and serotonin metabolites in the nucleus accumbens as a function of time post administration of clavulanic acid.

DETAILED DESCRIPTION OF THE INVENTION

Figure 1:
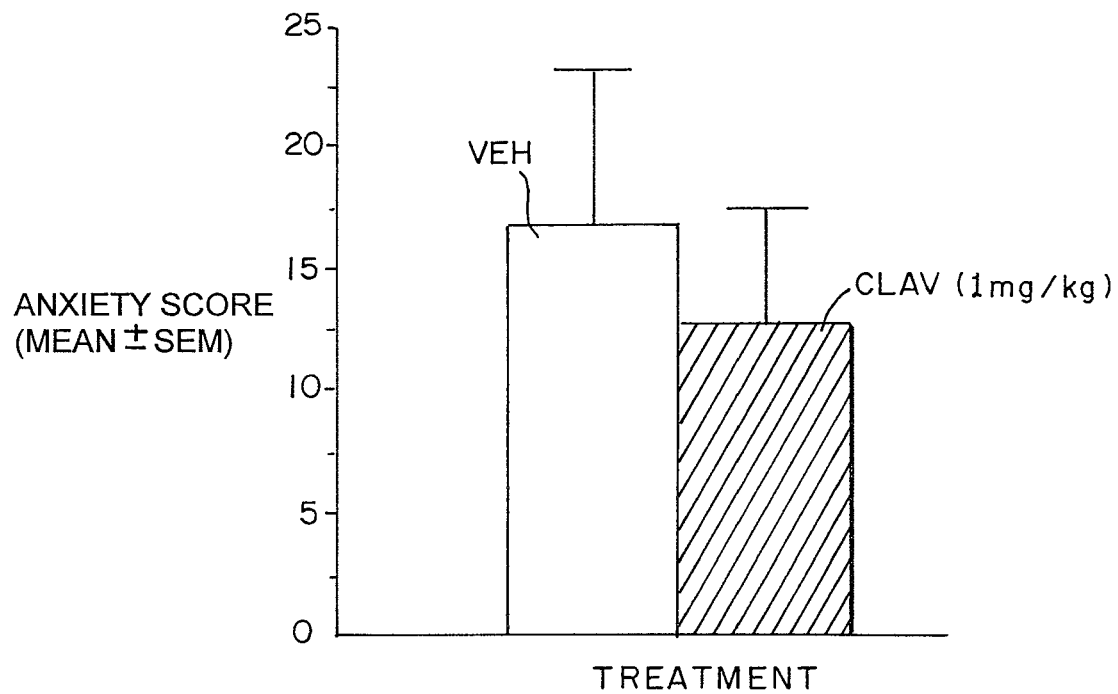
FIG. 1 is a bar graph showing anxiety scores for clavulanic acid administered to cotton-top tamarins.

There is provided in accordance with this invention a method for improving sexual function in a mammal suffering from or disposed to develop sexual dysfunction or otherwise in need of enhanced sexual function to promote normal or enhanced sexual function. Sexual dysfunction can be the result of any one or a combination of a wide variety of psychological or physiological patient conditions. Alternatively, sexual dysfunction can be a consequence of the temporal/local environment and physiological and psychological stress imposed by same. It is a condition that affects not only humans but also non-human mammals such as farm animals or zoo animals maintained in captivity.

As used herein, the term "sexual dysfunctions" includes sexual desire disorders, sexual arousal disorders, orgasmic disorders, sexual pain disorders, sexual dysfunction due to a general medical condition, substance-induced sexual dysfunction and sexual dysfunction not otherwise specified. These sexual dysfunctions may be further defined by the nature of the onset of the disorder: either lifelong type or acquired type; by the context in which the disorder occurs: either generalized type or situational type; and by the etiological factors associated with the disorder: either due to psychological factors or due to combined factors. Specifically, sexual desire disorders include hypoactive sexual desire disorder and sexual aversion disorder. Sexual arousal disorders include female sexual arousal disorder and male erectile disorder. Orgasmic disorders include female orgasmic disorder, male orgasmic disorder and premature ejaculation. Sexual pain disorders include dyspareunia and vaginismus. Sexual dysfunctions due to a general medical condition may result from neurological conditions (e.g. multiple sclerosis, spinal cord lesions, neuropathy and temporal lobe lesions), endocrine conditions (e.g. diabetes melitus, hypothyroidism, hypogonadal states and pituitary dysfunction), and vascular conditions and genitourinary conditions (e.g. testicular disease, Peyronie's disease, urethral infections, postprostatectomy complications, genital injury or infection, atrophic vaginitis, infections of the vagina and external genitalia, post-surgical complications such as episiotomy scars, shortened vagina, cystitis, endometriosis, uterine prolapse, pelvic infections and neoplasms). Substance-induced sexual dysfunction can occur in association with intoxication with the following classes of substance: alcohol; amphetamine (and amphetamine-like substances); cocaine; opioids; sedatives, hypnotic and anxiolytics; and other unknown substances. A decrease in sexual interest and orgasmic disorders may also be caused by prescribed medication including antihypertensives, histamine $H_2$-receptor antagonists, antidepressants, neuroleptics, anxiolytics, anabolic steroids, and antiepileptics. Painful orgasm has been reported with fluphenazine, thioridazine and amoxapine. Priapism has been reported with the use of chlorpromazine, trazodone and clozapine, and following penile injections of papaverine or prostaglandin. Selective serotonin reuptake inhibitors may cause decreased sexual desire or arousal disorders.

Also, as used herein, the term "sexual dysfunctions" includes any of the aforementioned sexual dysfunctions, including loss of libido, resulting from other medical conditions, most especially resulting from depression and/or anxiety. As used herein, the term "treatment" refers both to the treatment to promote normal or enhanced sexual function and to the prevention or prophylactic therapy of the aforementioned conditions.

In a related aspect of the invention it has been found that administration of β-lactamase inhibitors and other compounds capable of inhibiting penicillin-binding protein and structurally related mammalian enzymes activate serotonin and/or dopamine neurotransmission in the brain. Thus in accordance with another embodiment of the invention there is provided a method of activating serotonin and/or dopamine neurotransmission in the brain of a mammal. The method comprises the step of administering to said mammal a serotonin and/or dopamine neurotransmission enhancing amount of a compound selected from a β-lactamase inhibitor, a penicillin sulfoxide, a penicillin sulfone, and a cephalosporin or a cephalosporin analog or derivative of the formula

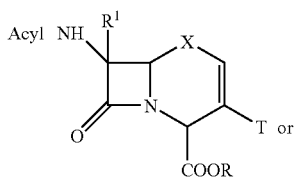

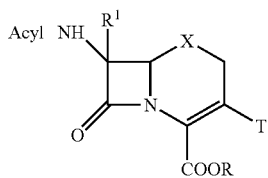

wherein X is S, SO, SO$_2$, O, CR$_2$, R$_3$, wherein R$_2$ and R$_3$ are independently hydrogen or C$_1$-C$_4$ alkyl, R is hydrogen, a salt forming group or an active ester forming group; R$^1$ is hydrogen or C$_1$-C$_4$ alkoxy, T is C$_1$-C$_4$ alkyl, halo (including chloro, fluoro, bromo and iodo), hydroxy, O(C$_1$-C$_4$)alkyl, or —CH$_2$B wherein B is the residue of a nucleophile B:H, and acyl is the residue of an organic acid Acyl OH.

In still another related aspect of the invention there is provided a method for using such compounds for the preparation of pharmaceutical formulations useful for activating serotonin and/or dopamine neurotransmission in the brain. Such formulations are expected to be effective in the treatment of numerous disease states having a neurological dysfunction etiology. Such disease states include but are not limited to addiction, obesity, and schizophrenia.

In still one other embodiment of the invention there is provided a method for improving sexual function in a mammal suffering from or disposed to develop sexual dysfunction or otherwise in need of enhanced sexual function. The method comprises the step of administering to said mammal a compound selected from the group consisting of a β-lactamase inhibitor, a penicillin, a penicillin sulfoxide, a penicillin sulfone, and a cephalosporin or a cephalosporin analog of the formula

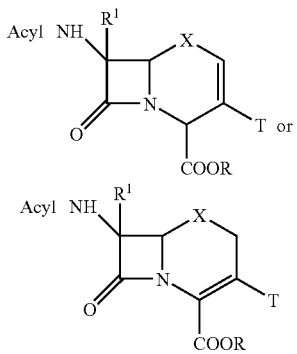

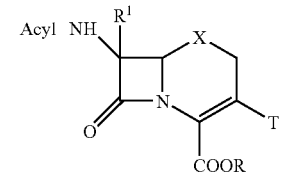

wherein X is S, SO, SO$_2$, O, CR$_2$, R$_3$, wherein R$_2$ and R$_3$ are independently hydrogen or C$_1$-C$_4$ alkyl, R is hydrogen, a salt forming group or an active ester forming group; R$^1$ is hydrogen or C$_1$-C$_4$ alkoxy, T is C$_1$-C$_4$ alkyl, halo (including chloro, fluoro, bromo and iodo), hydroxy, O(C$_1$-C$_4$)alkyl, or —CH$_2$B wherein B is the residue of a nucleophile B:H, and acyl is the residue of an organic acid Acyl OH.

The method can be utilized in both male and female patients and is preferably carried out with compounds as specified that are without clinically significant antimicrobial activity, more preferably compounds that are substantially devoid of antimicrobial activity.

One group of compounds useful in accordance with the present invention are β-lactamase inhibitors. There are many compounds that are reported in the literature to exhibit the capacity to inhibit bacterial β-lactamase activity. Such is typically measured by the compound's ability to inhibit the rate of hydrolysis of a penicillin or cephalosporin substrate by 50%, either with or without preincubation. Techniques for assessing or assaying β-lactamase inhibition and inhibition of other enzyme activity are well known in the art.

Most known β-lactamase inhibitors are compounds which themselves comprise a β-lactamase ring structure. Both the patent and non-patent art are replete with reference to such compounds, their preparation, and their mechanism of action. Inhibition of bacterial β-lactamase can occur either by an irreversible mechanism or via a reversible mechanism involving a transient inhibited intermediate in which the β-lactamase inhibitor binds to and thus blocks the active site on the β-lactamase molecule. β-lactamases can be inhibited irreversibly by a β-lactamase inhibitor which competitively or preferentially binds to the active site on the β-lactamase molecule where it effectively acylates the β-lactamase as a first step in deactivating the enzyme.

Exemplary of known β-lactamase inhibitors in commercial use are clavulanic acid, sulbactam, and tazobactam. Other known β-lactamase inhibitors include derivatives or analogs of clavulanic acid including deoxyclavulanic acid, isoclavulanic acid, 9-deoxyclavulanic acid, 9-amino deoxyclavulanic acid, and other clavulanic acid derivatives such as those wherein the 9-hydroxy group has been chemically modified (e.g. as an acetate, n-methyl carbamate, methyl ether, benzyl ether, or thiomethyl ether). Sulbactam has been used to prepare prodrugs, for example, sultamacillin which is absorbed from the gastrointestinal tract and then hydrolyzed into sulbactam and ampicillin. Other known β-lactam containing compounds known to possess β-lactamase inhibitor properties include olivanic acids and thienamycin of the carbapenem family of novel naturally occurring β-lactam antibiotics and sultamicillin and aztreonam.

One preferred β-lactamase inhibitor for use in accordance with the present invention is clavulanic acid. It has only weak, though broad spectrum antibacterial activity, and it has a long record of safe use as a β-lactamase inhibitor in commercially available combinations with amoxycillin and ticarcillin. Moreover, it exhibits good oral adsorption and transport across the blood-brain barrier into the cerebral spinal fluid. β-lactamase inhibitors can be administered in accordance with this invention as their pharmaceutically acceptable salts or as bioactive esters which hydrolyze to provide therapeutic concentrations of the β-lactamase inhibitor upon patient administration.

Effective dosages of the β-lactamase inhibitors when used in accordance with the method of this invention depends on patient condition and the method of administration. Animal tests indicate that clavulanic acid is effective when administered intraperitoneally at a dose of about 1 μg/kg to about 50 μg/kg. Parenteral doses of β-lactamase inhibitors when used in accordance with this invention range from about 0.02 to about 20 mg/kg. Oral dosage levels are typically higher, ranging from about 0.05 mg/kg to about 50 mg/kg. The dosage levels can be adjusted higher or lower by the attending physician depending on patient condition and the observed clinical response to the initial dosage. Treatment in accordance with this invention typically includes one to four daily doses of β-lactamase inhibitor. Formulation of the inhibitor into controlled release dosage forms (either for parenteral or oral use) enables effective once or twice a day dosage protocols.

In addition to β-lactamase inhibitors, other β-lactam-containing compounds, i.e., compounds having a β-lactam ring system, can be used in accordance with this invention, generally to activate or enhance serotonin and dopamine neurotransmission, and more specifically to improve sexual function or to treat certain other disease states responsive to activation of serotonin and dopamine neurotransmission.

Examples of such compounds are β-lactam antibiotics, such as penicillins and cephalosporins and derivatives, for example, their sulfoxides or sulfones, and analogs thereof, such as the art recognized 1-oxa-1-dethiacephems and the 1-carba-1-dethiacephems. The prior art is replete with reference to many of such compounds and their method of synthesis/preparation.

Penicillin sulfoxides or sulfones useful in this invention are of the general formula

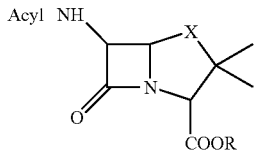

wherein X is SO or $SO_2$ and R and Acyl are as defined above.

The cephalosporin/cephalosporin analogs/derivatives useful in accordance with this invention include both 2-cephem compounds of the formula

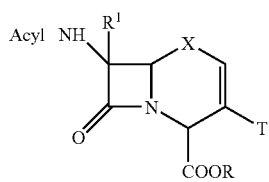

and 3-cephem compounds of the formula

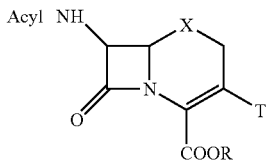

wherein X is S, $SO_2$, O, $CR_2$, $R_3$, wherein $R_2$ and $R_3$ are independently hydrogen or $C_1$-$C_4$ alkyl, R is hydrogen, a salt forming group or an active ester forming group; $R^1$ is hydrogen or $C_1$-$C_4$ alkoxy, T is $C_1$-$C_4$ alkyl, halo (including chloro, fluoro, bromo and iodo), hydroxy, $O(C_1$-$C_4)$alkyl, or —$CH_2B$ wherein B is the residue of a nucleophile B:H, and Acyl is the residue of an organic acid Acyl OH.

Variations of substituents "Acyl," "$R^1$" and "T" have been the subject of years of cephalosporin research which produced many commercially significant cephalosporin antibiotics. While the nature of such substituent can impact the biological activity of the respective compounds, the nature of such substituents is not the focus of the present invention.

One group of compounds for neurotherapeutic use herein are β-lactam antibiotics including penicillins, cephalosporins and monocyclic and bicyclic analogs or derivatives thereof. Commercially available antibiotics for use in the present method and use include penams, cephems, 1-oxa-1-dethia cephems, clavams, clavems, azetidinones, carbapenams, carbapenems and carbacephems.

In one embodiment of this invention the β-lactam ring containing compounds for us in this invention are without clinically significant antibiotic activity, and ideally, they are substantially devoid of biological activity. Such compounds include, for example, the 2-cephem compounds generally and as well the 2- and 3-cephem sulfoxide (X=SO) and sulfone derivatives (X=$SO_2$) and penicillin sulfoxide and sulfone derivatives.

The β-lactam compounds for use in this invention having a carboxylate functional group can be administered as its pharmaceutically acceptable salt or in the form of an in vivo hydrolysable (active) ester group.

Examples of suitable in vivo hydrolysable (active) ester groups include, for example, acyloxyalkyl groups such as acetoxymethyl, pivaloyloxymethyl, β-acetoxyethyl, β-pivaloyloxyethyl, 1-(cyclohexylcarboonyloxy)prop-1-yl, and (1-aminoethyl)carbonyloxymethyl; alkoxycarbonyloxyalkyl groups, such as ethoxycarbonyloxymethyl and alpha-ethoxycarbonyloxyethyl; dialkylaminoalkyl groups, such as ethoxycarbonyloxymethyl and β-ethoxycarbonyloxyethyl; dialkylaminoalkyl especially di-lower alkylamino alkyl groups such as dimethylaminomethyl, dimethylaminoethyl, diethylaminomethyl or diethylaminoethyl: 2-(alkoxycarbonyl)-2-alkenyl groups such as 2-(isobutoxycarbonyl)pent-2-enyl and 2-(ethoxycarbonyl)but-2-enyl; lactone groups such as phthalidyl and dimethoxyphthalidyl; and esters linked to a second β-lactam compound.

Suitable pharmaceutically acceptable salts of β-lactam compounds used in this invention include metal salts, e.g. aluminum, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)amine, cycloalkylamines such as dicyclohexylamine, or with procaine, dibenzylamine, N,N-dibenzylethylenediamine, 1-ephenamine, N-methylmorpholine, N-ethylpiperidine, N-benzyl-β-phenethylamine, dehydroabietylamine, N,N'-bisdehydro-abietylamine, ethylenediamine, or bases of the pyridine type such as pyridine, collidine or quinoline, or other amines which have been used to form salts with known penicillins and cephalosporins. Other useful salts include the lithium salt and silver salt.

The amount of β-lactam compounds used to form the pharmaceutical composition is that amount effective to provide upon delivery by the intended route of administration, an effective concentration of the compound in neuronal tissue. Typically they are administered at a dose of about 0.01 mg/kg to about 10 mg/kg. Parenteral dosage forms typically can contain about 0.5 to about 50 mg/dose or 2- to 3-fold that amount when formulated in a controlled release parenteral dosage form, while oral dosage forms can typically contain about 1 to about 200 mg of the active compound.

Compounds for therapy in accordance with this invention be formulated/combined with one or more pharmaceutically acceptable carriers and may be administered, for example, orally in such forms as tablets, capsules, caplets, dispersible powders, granules, lozenges, mucosal patches, sachets, and the like. In such formulations a the active compound is combined with a pharmaceutically acceptable carrier, for example starch, lactose or trehalose, alone or in combination with one or more formulation excipients and pressed into tablets or lozenges or filled into capsules. Optionally, dosage forms intended for oral ingestion administration such as tablets, caplets or capsules can be enterically coated to minimize hydrolysis/degradation in the stomach. In another embodiment the dosage form is formulated for oral administration, and is formed as a prolonged release dosage form using art-recognized formulation techniques for release the compound over a predetermined period of time.

Topical dosage forms, including transdermal patches, intranasal and suppository dosage unit formulations containing the active compound and conventional non-toxic pharmaceutically acceptable carriers, adjuvants and vehicles adapted for such routes of administration can also be used.

The pharmaceutical compositions suitable for injectable use in accordance with this invention include sterile aqueous solutions or dispersions and sterile powders or lyopholysates for the extemporaneous preparation of sterile injectable solutions or dispersions. The dosage forms must be sterile and it must be stable under the conditions of manufacture and storage. The carrier for injectable formulations is typically water but can also include ethanol, a polyol (for example, glycerol, propylene glycol and liquid polyethylene glycol), mixtures thereof, and vegetable oil.

Parenteral dosage forms useful in accordance with the present invention can also be formulated as injectable prolonged release formulations in which the active compound is combined with one or more natural or synthetic biodegradable or biodispersible polymers such as carbohydrates, including starches, gums and etherified or esterified cellulosic derivatives, polyethers, polyesters, polyvinyl alcohols, gelatins, or alginates. Such dosage formulations can be prepared for example in the form of microsphere suspensions, gels, or shaped polymer matrix implants that are well-known in the art for their function as "depot-type" drug delivery systems that provide prolonged release of the biologically active components. Such compositions can be prepared using art-recognized formulation techniques and designed for any of a wide variety of drug release profiles.

Screening Clavulanic Acid (CLAV) for Anxiolytic Activity in Non-Human Primates

The cotton-top tamarin (*Saguinus oedipus*) is listed as an endangered species with only 1-3 thousand remaining in the rain forests of Colombia. This monkey has a high stress temperament, making it difficult to breed and rear in captivity (Snowdon et al., 1985). Captive tamarins have the highest prevalence of stress-induced colitis and colon cancer of any monkey studied (Clapp et al., 1988). The stress of captivity contributes to the onset of inflammatory bowl disease since this condition is extremely rare in wild populations (Wood et al., 1998; Wood et al., 2000) and remission occurs when captive monkeys are returned to the environmental conditions of the natural habitat (Wood et al., 1995). If orally administered CLAV could reduce anxiety and stress in these non-human primates there is a strong likelihood the drug would be effective when tested in humans. Dr. Charles Snowdon, Department of Psychology, University of Wisconsin at Madison was enlisted to design a study using tamarins to test the anxiolytic activity of CLAV. Dr. Snowdon is a world expert in tamarin behavior with over twenty peer-reviewed publications in the field. Dr. Snowdon has studied tamarins in the wild (Savage et al., 1997) and in the semi-natural environment of his labs at Madison (Ginther et al., 2000).

Methods

Eight male/female pairs of tamarins with long standing pair bonds were tested following oral treatments of CLAV and vehicle (VEH) control. There were no offspring since males were vasectomized. Both members of a pair received the same treatments at the same times. Each animal served as its own control being tested both with CLAV or VEH one week apart. The treatment schedule was counter-balanced. CLAV was dissolved in water and dispensed onto a small cookie in a volume of 100 μl. A single CLAV cookie was given to each member of a pair at an approximate dose of 1 mg/kg body weight. Animals were given three CLAV cookies each day for two consecutive days. The $1^{st}$ cookie was given at 8:00 AM prior to the morning feeding, the $2^{nd}$ at 11:00 AM prior to the noon feeding and the $3^{rd}$ at 2:00 PM prior to the late afternoon snack. All animals were scored for anti-anxiety activity 60 min after the $3^{rd}$ treatment on the second day.

This treatment regimen of three doses each day for two consecutive days was chosen to acclimate the animals to the treatment procedure (day 1) and to achieve steady-state blood concentration before testing (day 2). A pharmacokinetic assessment of CLAV was run by IVEDCO (Irving Tex.) which estimated an oral dose of 1 mg/kg every three hrs would produce steady-state levels yielding an average plasma concentration of 2.5 μg/ml at the time of testing. Since the CSF/plasma ratio is 0.25 the estimated concentration in the brain would be around 0.3 μM. Given the rate of clearance of CLAV, treatments from day 1 should not have contributed to blood levels of drug on day 2.

Two observers blind to the treatment independently scored behavioral activity. To elicit anxious/stressful behavior a novel object was placed into the home cage. A different novel object was used for each test session and the object presentation was counter-balanced. Following the presentation of the novel object animals were scored for a duration of 15 min for: 1) latency to approach and latency to touch the object, 2) time spent in contact or proximity with the object, 3) face and head movement (frowns, head shakes and head cocks that reflect tension), 4) scratching (a validated measure of anxiety in macaques), 5) piloerection (autonomic stress response), and 6) visual scanning (nervous vigilance). On the first test session, it was noted that males treated with CLAV showed a high incidence of penile erection, hence the number of erections; mounts and female solicitations were also scored.

Results

There was no significant difference between treatments in latency to approach or latency to touch the novel object.

Neither was there any difference in time spent in proximity to the object. However, using the combined measures of anxious/nervous behaviors (3, 4, 5 & 6) there were significantly fewer of these behaviors following treatment with CLAV (12.7+4.8) than with VEH (16.8=6.4) (Wilcoxon t=28, n=15 p<0.05) (FIG. 1). There were no gender differences in drug response.

Figure 2:
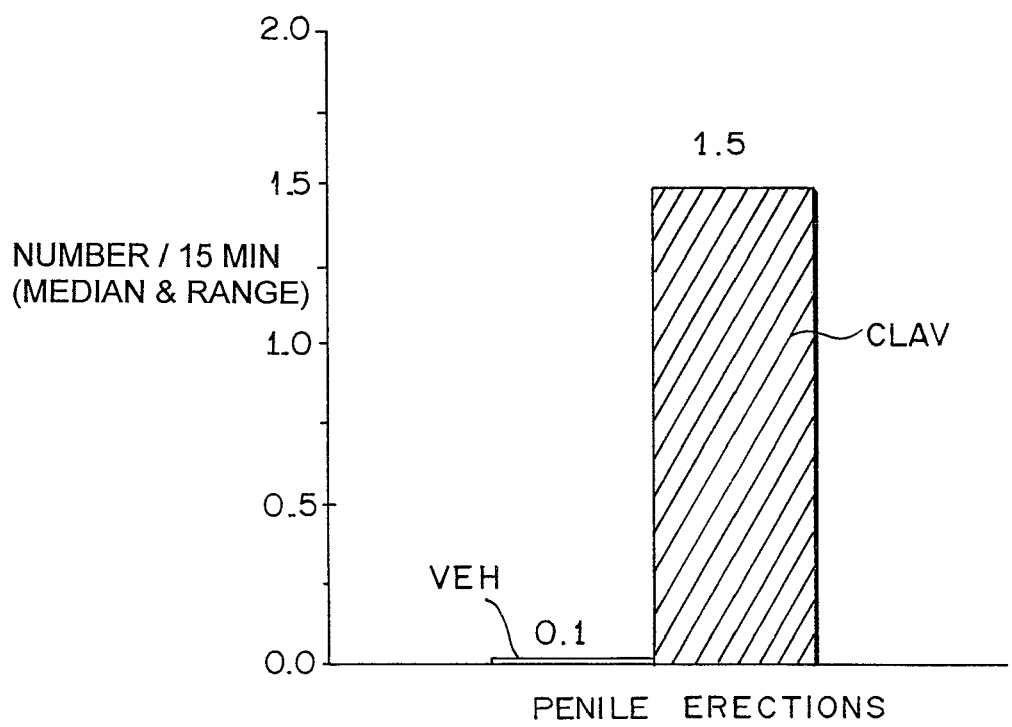
FIG. 2 is a bar graph showing the effect of clavulanic acid on sexual arousal in cotton-top tamarins.
Figure 3:
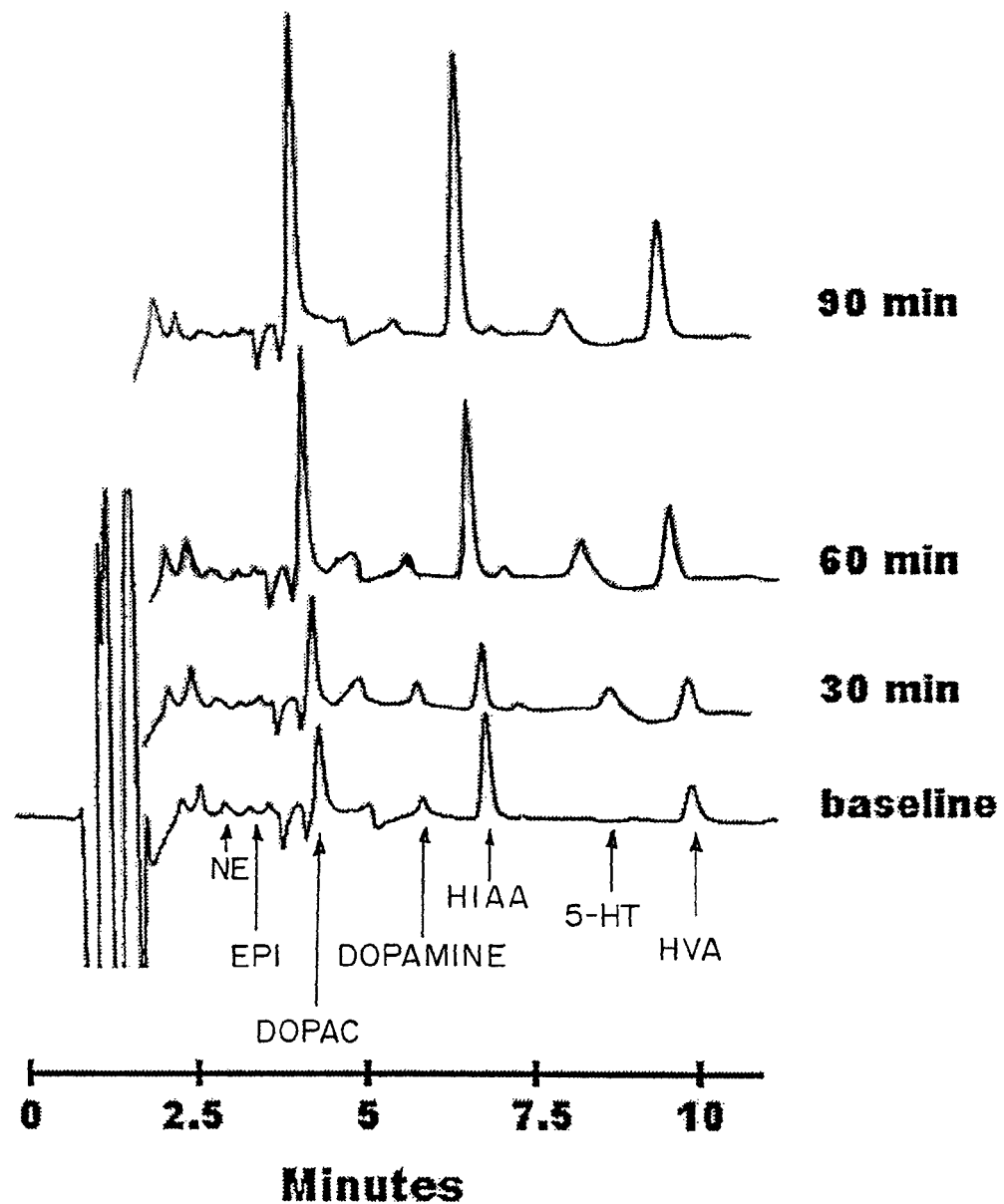
FIG. 3 illustrates several chromatograms from HPLC electrochemical detection of dialysate samples collected in the nucleus accumbens in a test animal following intraperitoneal administration of 10 μg/kg of clavulanic acid. Retention times for norepinephrine (NE), epinephrine (Epi), dopamine metabolite DOPAC, dopamine, serotonin metabolite HIAA, serotonin (5-HT), and homovanillic acid (HVA) are indicated.

The unexpected result was the increase in erections by males. All eight males showed at least one erection in 15 min when treated with CLAV while only three of these eight showed erections with VEH (FIG. 2). The mean was 2.25 erections in 15 min with CLAV and 0.37 with VEH. Cotton-top tamarins in captivity show an average base rate of 1.5 erections per hour during their active diurnal period, a rate comparable to VEH treatment (Snowdon personal communication). Animals treated with CLAV show a rate of 9.0 erections per hour. These results were significant by a Wilcoxon test (t=0, n=7, p<0.02). Two of the eight females showed solicitation behaviors with CLAV treatment while no females showed solicitation with VEH. There was no significant difference in mounting behavior between CLAV and VEH treatments.

Summary

Clavulanic acid given orally at a dose of 1 mg/kg reduced measures of anxiety in male/female pairs of cotton-top tamarins. The time course of action was very rapid and appeared in less than two days of treatments. It is possible the effect could have been observed in 60 min after a single dose of CLAV, as is the case in rodent studies. Studies are presently underway to ascertain the minimal oral dose of CLAV and the shortest time course that significantly reduces anxiety in tamarins. Nonetheless, the time-course noted in these studies is far better than the selective serotonin reuptake inhibitors (SSRIs), e.g., fluoxetine and sertraline that are becoming more prevalent in the treatment of anxiety disorders. SSRIs take several days to weeks before achieving clinical efficacy. In addition, the SSRIs suppress libido contributing to sexual dysfunction (Rothschild 2000). CLAV not only reduced anxiety in cotton-top tamarins, but it also increased sexual arousal as indicated by the increased rate of penile erections. The mechanism for this biological effect is unknown. CLAV could have a direct psychogenic effect on libido or the enhanced sexual arousal could be secondary to a reduction in stress. The latter hypothesis is not unreasonable since stress is one of the major factors contributing to sexual dysfunction (Smith 1988). The anxiety disorder, PTSD or post-traumatic stress disorder has a particularly high incidence of sexual dysfunction (Kotler et al., 2000). Studies in rats show that long-term psychological stress impairs sexual behavior, a result associated with a decrease in monoamine activity in the brain (Sato et al., 1996). Enhancing monoamine activity restores normal sexual behavior following chronic stress. It was determined to gather data to assess whether CLAV is increasing sexual arousal in tamarins by increasing monoamine activity in the brain.

Using CLAV to reduce anxiety and enhance sexual arousal in the cotton-top tamarin, a species whose existence is jeopardized by its high stress temperament, is very significant. This drug may have a role in animal husbandry to help in the breeding and rearing of endangered species held in captivity. More importantly, the fact CLAV has anxiolytic activity in the tamarin holds the promise the CLAV and other β-lactamase inhibitors and other β-lactam compounds may be an effective therapeutic for the treatment of anxiety disorders in humans and even stress-related gastrointestinal disease.

While CLAV does not appear to bind to any of the well known signaling receptors or transporters, is clearly altering brain chemistry in some way, either by neurogenic enzyme inhibition or by interaction with a still unrecognized receptor system, to achieve anxiolytic activity. To test this hypothesis, extracellular neurotransmitter levels in the area of the nucleus accumbens were assessed with microdialysis following CLAV treatment. The accumbens is part of the limbic forebrain best now for its association with the pathophysiology of schizophrenia and drug addiction but also thought to be involved in sensitization to early life trauma leading to the anxiety disorder PTSD or post traumatic stress disorder (Chamey and Bremner 1999).

Experimental Procedure

Ten male, Sprague Dawley rats were anesthetized with sodium pentobarbital (50 mg/kg) and implanted with a unilateral microdialysis guide cannula aimed at the nucleus accumbens. Two days after recovery from surgery a microdialysis probe (2 mm) was lowered to the area and connected to an infusion pump through Tygon tubing. The dialysate was artificial CSF at pH 7.4 delivered at a flow rate of 2 μl/min. The first 120 min of dialysate will be discarded. Thereafter, samples were collected at 30 min intervals prior to and following IP CLAV treatment (10 μg/kg). Samples were collected into microfuge tubes containing 5 μl of 0.16 N perchloric acid to stabilize catecholamines. At the end of the study, animals were sacrificed and the brains prepared for histology to verify the site of the microdialysis probe.

Results

Figure 4A:
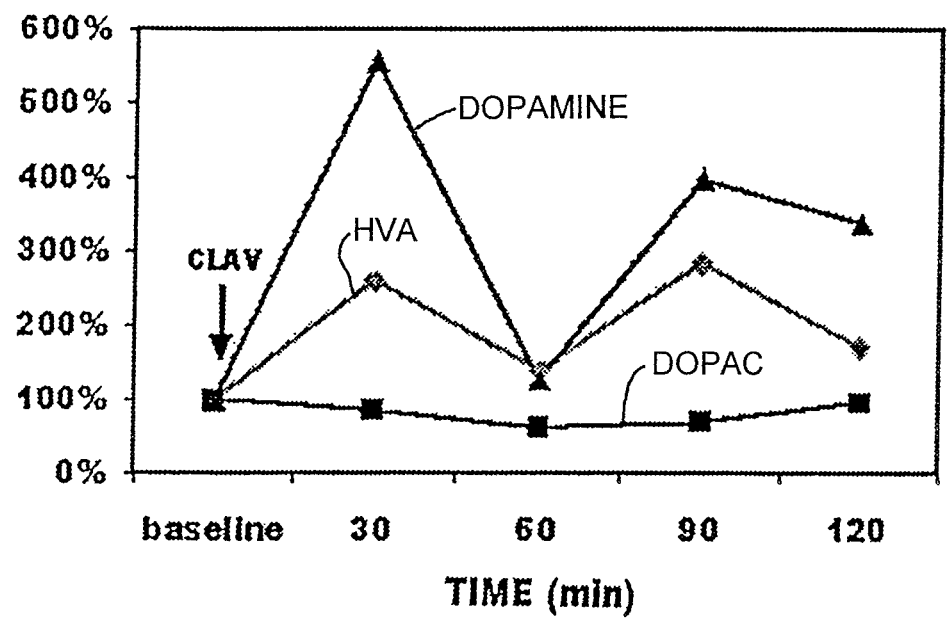
FIGS. 4A and 4B are graphic representations of the concentrations of neurotransmitters in the nucleus accumbens of a test animal (AC-1) as a function of time from administration of clavulanic acid.
Figure 4B:
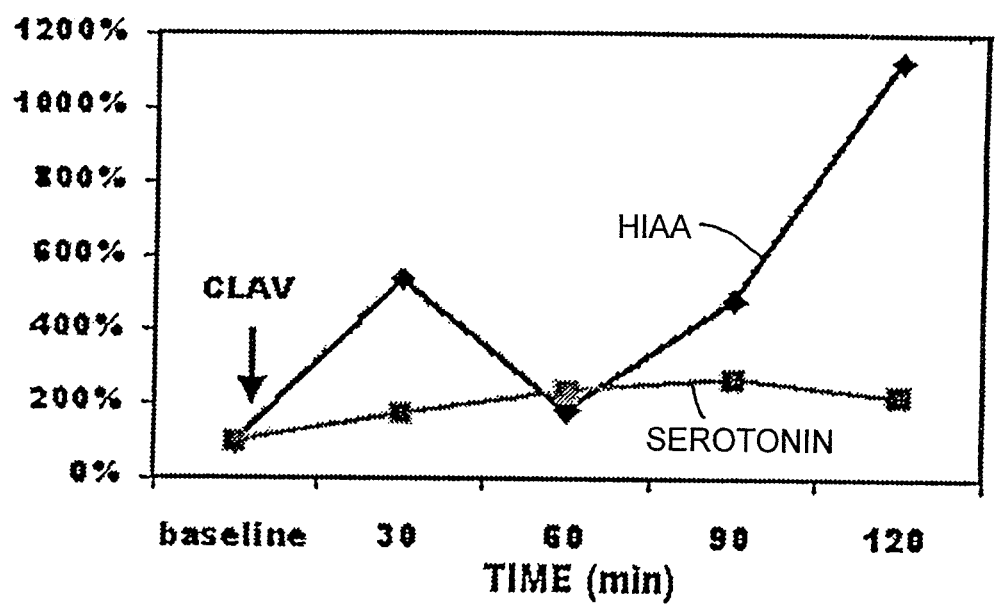
Figure 5A:
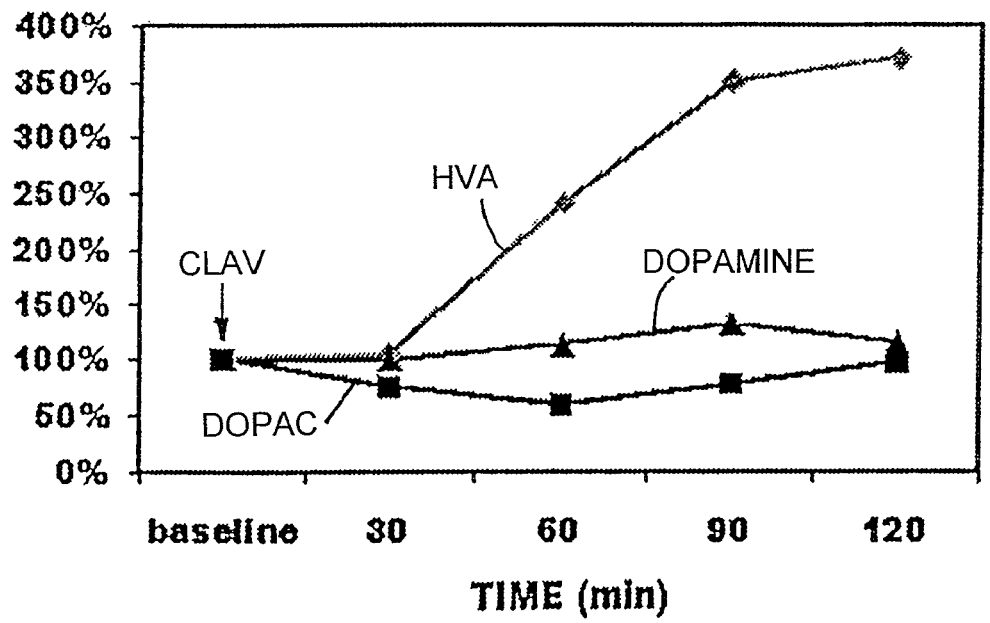
FIGS. 5A and 5B are similar to FIGS. 4A and 4B but the data is that from a second test animal (AC-2)
Figure 5B:
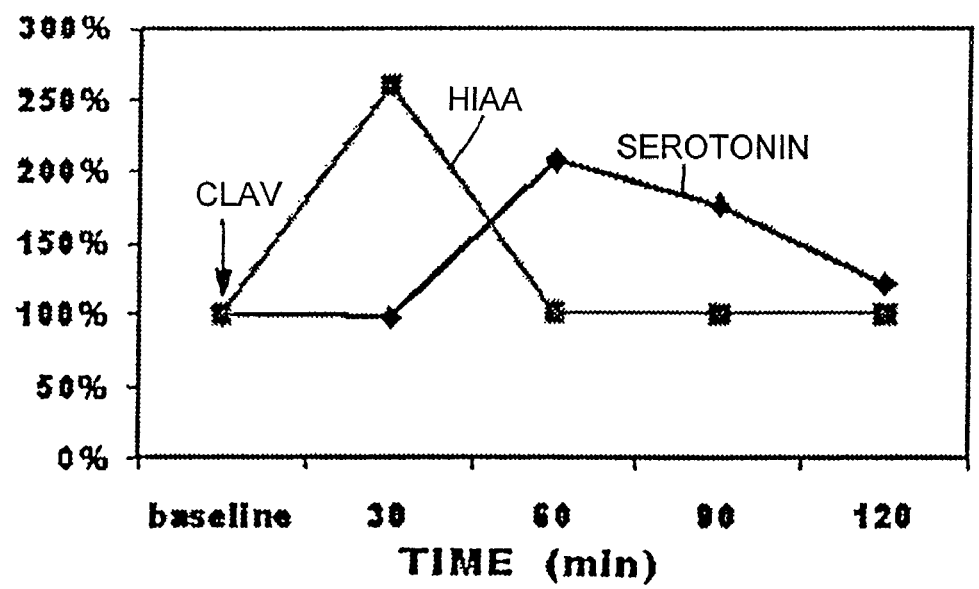
Figure 6A:
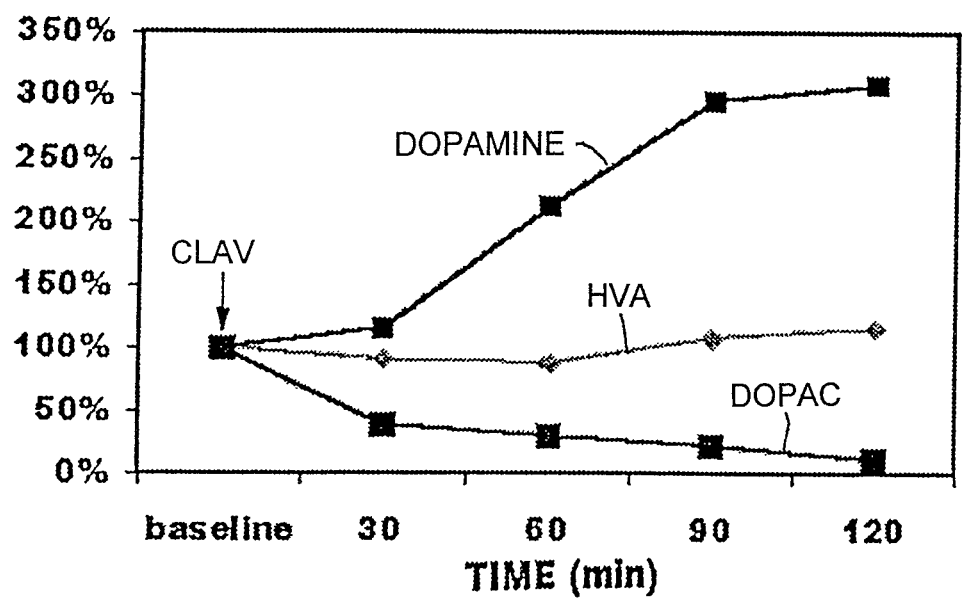
FIGS. 6A and 6B are similar to FIGS. 4A and 4B except they depict test data from a third test animal (AC-3)
Figure 6B:
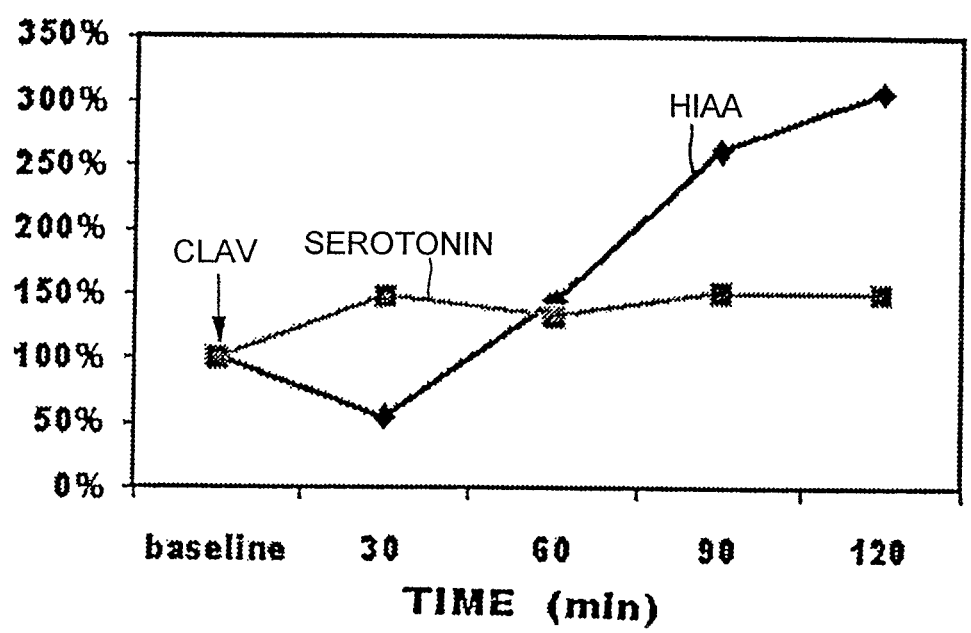
Figure 7A:
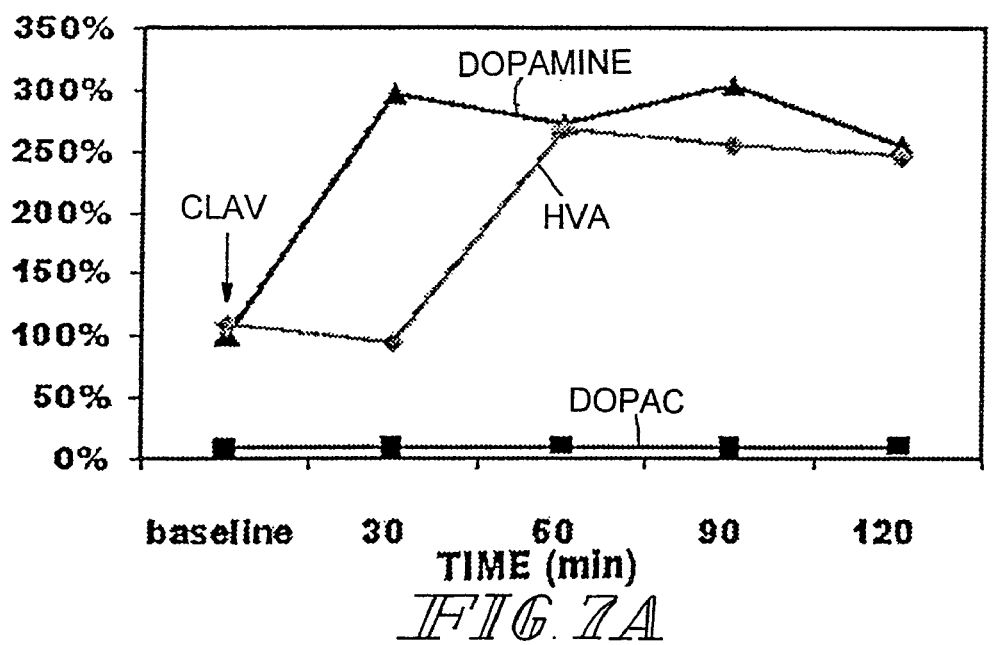
FIGS. 7A and 7B are similar to FIGS. 4A and 4B except that they depict test data from a fourth test animal (AC-4)
Figure 7B:
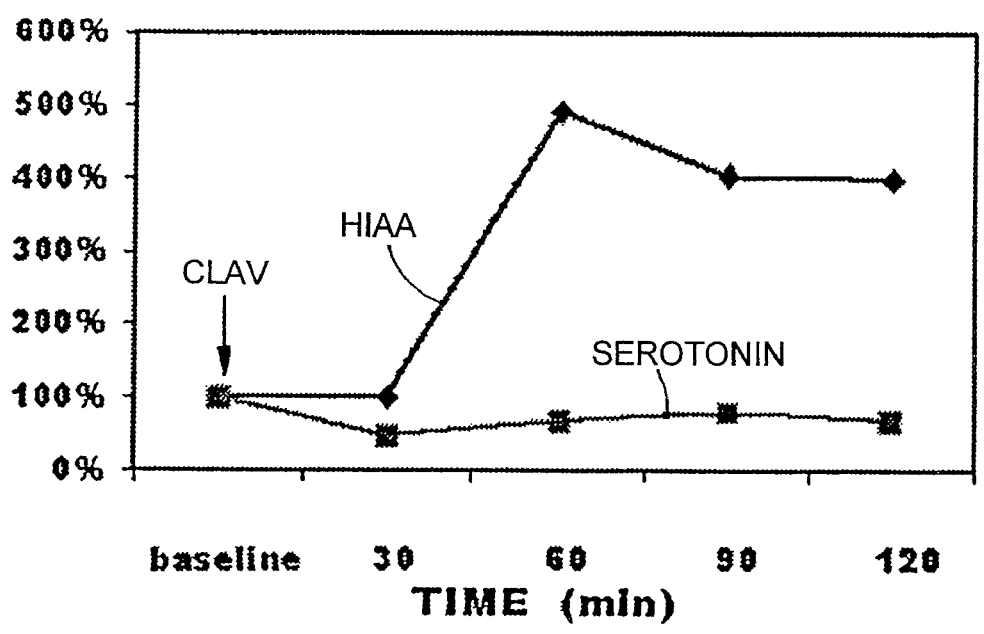

Five of the ten animals studied showed the microdialysis probe positioned in the nucleus accumbens (AC). In these five animals (AC-1 through AC-5), electrochemical detection revealed a time-dependent change in molecules associated with enhanced neurotransmission of the serotonin and dopamine systems (FIGS. 4A, B-8A, B). For example, FIG. 4A is a composite of chromatograms showing changes in monoaminergic molecules prior to and following CLAV treatment in animals AC-1. Over time there is an increase in extracellular levels of serotonin concomitant with a robust increase in the serotonin metabolite 5-hydroxyindoleacetic acid (HIAA). While there is a modest decrease in dopamine there is a robust increase in its metabolites homovanillic acid (HVA) and 3,4-dihydroxyphenylacetic acid (DOPAC). These increases in metabolite levels most probably reflect increased neurotransmission of serotonin and dopamine. However, it is possible that some of the metabolism is not directly coupled to the release of the neurotransmitters (Westemick, 1985).

Figure 8A:
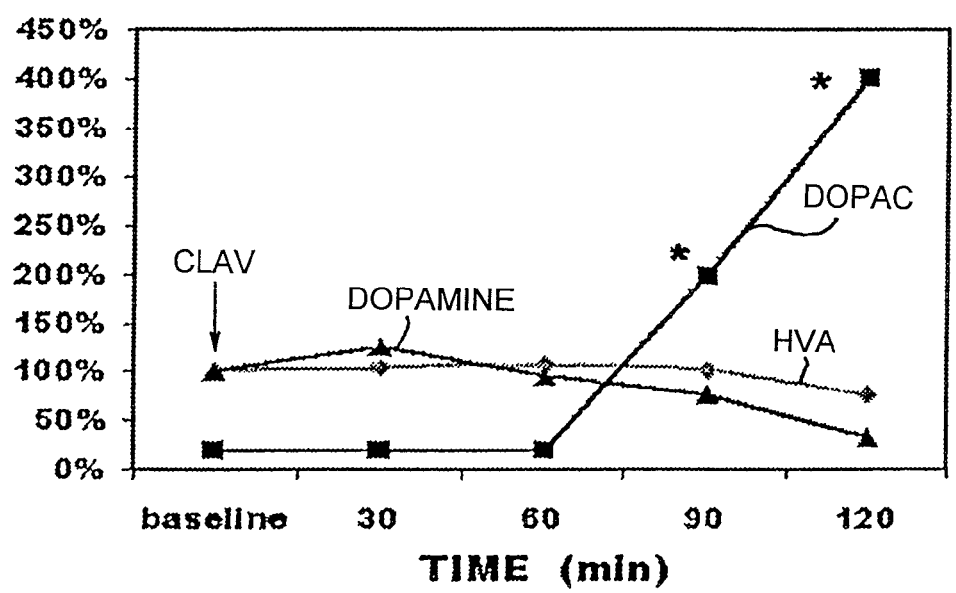
FIGS. 8A and 8B are also similar to FIGS. 4A and 4B except that they depict test results from a fifth test animal (AC-5).
Figure 8B:
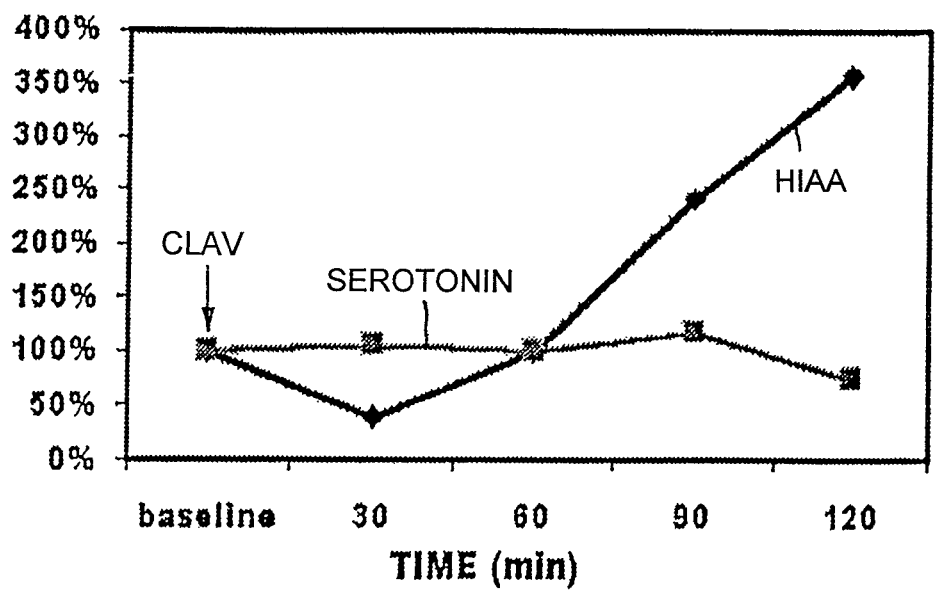

The percent change from control values for these monoaminergic molecules for animals AC-1 through AC-5 are shown in FIGS. 4A, B-8A, B, respectively. The change in serotoninergic molecules was fairly consistent. In all cases, animals showed increases in the serotonin metabolite HIAA of 100%-1000% above baseline (30-50 pm/ml) following CLAV treatment. The changes in serotonin levels were more variable with three cases showing an increase of 50%-100% above baseline (undetectable—5 pm/ml), one no change, and the other a modest decrease. The change in dopaminergic molecules was also fairly consistent. In four of five animals there was an increase in the major dopamine metabolite HVA of 15%-350% above baseline (50-105 pm/ml) following CLAV treatment. The exception, animal AC-5 (FIG. 8B) showed high baseline levels of HVA that remained stable over the course of the study; however, levels of the other dopamine metabolite DOPAC rose. In three of five animals dopamine levels increased 50%-450% above baseline (0.5-0.7 pm/ml) following CLAV treatment, while the other two decreased.

DOPAC levels only rose in two cases AC-3 and AC-5, the same animals that showed decreases in dopamine.

Animals with the microdialysis probe outside the nucleus accumbens showed little if any changes in dopamine and serotonin neurotransmission following CLAV treatment. These sites were the lateral ventricle, bed nucleus of stria terminalis, head of the caudate, and ventrolateral thalamus.

Summary

These microdialysis studies indicate CLAV increases serotonin and dopamine neurotransmission in the nucleus accumbens. Recent advances in the treatment of anxiety disorders have focused on the activation of the serotonin neurotransmission (Feighner 1999). Given the work in this area it is not surprising that CLAV's release of serotonin is accompanied by robust anti-anxiety behavior in animal models. Interestingly, the enhanced monoaminergic neurotransmission with CLAV treatment may explain, in part, the increased sexual arousal in the stress-prone cotton-top tamarin.

The activation of serotonin and dopamine neurotransmission in the nucleus accumbens raises the possibility that CLAV may be used to treat drug addiction, obesity, and schizophrenia. Work by scientists at the National Institute of Drug Abuse and the National Institute of Diabetes and Digestive and Kidney Diseases have shown that the combined administration of amphetamine analogs phentermine and fenfluramine (PHEN/FEN) increases extracellular dopamine and serotonin levels in the nucleus accumbens of rats (Baumann et al., 2000). PHEN/FEN is a an effective pharmacotherapy for obesity (Weintraub et al., 1984) and in open clinical trials decreased cocaine craving, alleviated withdrawal symptoms and prolonged drug abstinence (Rothman et al., 1994). Scientists at the National Institutes of Health concluded drugs with a similar mechanism to PHEN/FEN causing increased neurotransmission of serotonin and dopamine in the nucleus accumbens may have utility in the treatment of substance abuse and obesity.

Work by scientists from Eli Lilly and Company used microdialysis and ex vivo tissue analysis of prefrontal cortex and nucleus accumbens to evaluate the mechanism of action of a metabotropic glutamate receptor agonists being developed for the treatment of psychosis (Cartmell et al., 2000a; 2000b). Atypical antipsychotics like risperidone increase dopamine and serotonin neurotransmission in the prefrontal cortex and nucleus accumbens (Cartmell et al., 2000b; Hertel et al. 1997). The Lilly scientists found that activation of metabotropic glutamate receptors has a similar mechanism elevating DOPAC, HIAA and HVA in these brain areas.

How CLAV alters serotonin and dopamine neurotransmission is still unknown. Neither the monoamine transporters nor the degradative enzyme monoamine oxidase A show binding to CLAV. Antagonism of any of these receptor proteins would be expected to alter extracellular levels of monoaminergic molecules. It would appear CLAV enhances serotonin and dopamine neurotransmission indirectly by suppressing or activating other neurotransmitter systems that regulate their activity. CLAV binding to proteolytic enzyme systems that regulate glutamate activity in the brain have been examined.

Pharmaceutical Formulations and Use

The following formulations are prepared using standard formulation techniques with a mass ratio of carrier to active compound of about 99:1 to about 30:1.

| Formulations | | | |
|---|---|---|---|
| β-lactamase inhibitor/dose (mg) | | Carrier | Dosage Form |
| I. | Clavulanic acid, potassium/30 | starch/maltose | capsule |
| II. | Clavulanic acid, sodium/50 | microcrystalline cellulose/trehalose | tablet |
| III. | Tazobactam/75 | saline | injectable |
| IV. | Tazobactam/125 | starch microspheres | injectable |
| V. | Clavulanic acid, potassium/150 | saline | injectable |
| VI. | Sulbactam/200 | saline | injectable |
| VII. | Sulbactam/250 | polylactide microspheres | injectable |
| VIII. | Cefsulodin/50 | starch microspheres | injectable |
| IX. | Moxalactam bis-indanyl ester/20 | microcrystalline cellulose | capsule |
| X. | Cefazolin/120 | saline | injectable |
| XI. | Cefazolin sulfoxide/10 | saline | injectable |
| XII. | Cephalexin sulfone/35 | polylactic acid microspheres | injectable |
| XIII | Cefaclor sulfoxide/75 | saline | injectable |

Formulation Use

A). A male patient suffering from erectile dysfunction is administered a dose of Formulation I about 1 hour before conjugal activity to improve sexual performance.

B). A female patient suffering from mild depression self-administers Formulation IX t.i.d. over a 2-week period to improve her libido.

C). A dog breeder administers Formulation V to his female and/or male canines to promote breeding activities.

D). A zoo keeper administers Formulation XI to male and female partners of a rare simian species to promote reproductive breeding of the animals.

What is claimed is:

1. A method for improving sexual function in a mammal suffering from sexual dysfunction or otherwise in need of enhanced sexual function, said method comprising the step of administering to said mammal a β-lactam compound capable of inhibiting the activity of a bacterial enzyme selected from β-lactamase or penicillin binding protein or a carboxypeptidase, where the β-lactam compound is administered in an amount therapeutically effective to treat the sexual dysfunction or enhance the sexual function of said mammal.

2. The method of claim 1 wherein the mammal is male.

3. The method of claim 2 wherein the sexual dysfunction is erectile dysfunction.

4. The method of claim 2 wherein the enhanced sexual function is the avoidance of premature ejaculation.

5. The method of claim 1 wherein the mammal is female.

6. The method of claim 5 wherein the enhanced sexual function is increased libido.

7. The method of claim 1 wherein the carboxy peptidase is carboxypeptidase E.

8. The method of claim 1 wherein the compound is a β-lactamase inhibitor.

9. The method of claim 1 wherein the compound is a β-lactam antibiotic.

10. The method of claim 1 wherein the compound is a cephalosporin sulfoxide or a cephalosporin sulfone.

11. The method of claim 1 wherein the compound is a cephalosporin or a cephalosporin analog or derivative of the formula

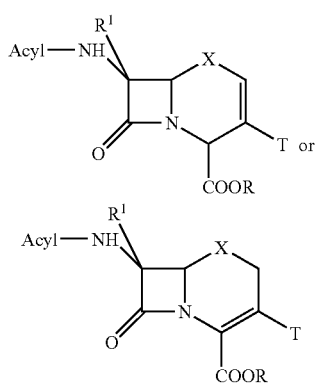

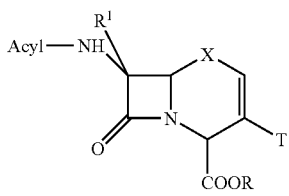

wherein X is S, SO, $SO_2$, O, or $CR_2R_3$, wherein $R_2$ and $R_3$ are independently hydrogen or $C_1$-$C_4$ alkyl; R is hydrogen, a salt forming group, or an active ester forming group; $R^1$ is hydrogen or $C_1$-$C_4$ alkoxy; and T is $C_1$-$C_1$ alkyl, a halogen, a hydroxy group, $O(C_1$-$C_4)$ alkyl, or —$CH_2B$, wherein B is a nucleophile residue.

12. The method of claim 1 wherein the compound is a cephem compound of the formula

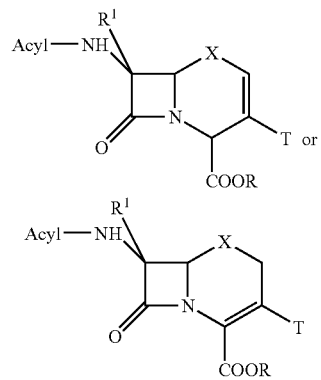

wherein X is S, SO, or $SO_2$; R is hydrogen, a salt forming group or an active ester forming group; $R^1$ is hydrogen or $C_1$-$C_4$ alkoxy; and T is $C_1$-$C_4$ alkyl, a halogen, a hydroxy group, $O(C_1$-$C_4)$ alkyl, or —$CH_2B$, wherein B is a nucleophile residue.

13. The method of claim 1 wherein the compound is a penicillin sulfoxide or penicillin sulfone.

14. The method of claim 1 wherein the compound is selected from the group consisting of clavulanic acid, tazobactam, sulbactam, thienamycin and analogs thereof, sultamicillin, aztreonam, and pharmaceutically acceptable salts and active esters thereof.

15. The method of claim 1 wherein the compound is clavulanic acid or a pharmaceutically acceptable salt or ester thereof.

16. The method of claim 1 wherein the compound is administered orally.

17. The method of claim 1 wherein the compound is administered sublingually or buccally.

18. The method of claim 1 wherein the compound is administered by inhalation.

19. The method of claim 1 wherein the compound is administered transdermally.

20. The method of claim 1 wherein the compound is administered parenterally.

21. The method of claim 1 wherein the amount is less than an antiobiotically effective amount.

22. A method for improving sexual function in a mammal suffering from sexual dysfunction or otherwise in need of enhanced sexual function, said method comprising the step of administering to said mammal a compound selected from the group consisting of a β-lactamase inhibitor, a penicillin, a penicillin sulfoxide, a penicillin sulfone, and a cephalosporin or a cephalosporin analog of the formula wherein X is S, SO, $SO_2$, O, or $CR_2R_3$, wherein $R_2$ and $R_3$ are independently hydrogen or $C_1$-$C_4$ alkyl; R is hydrogen, a salt forming group, or an active ester forming group; $R^1$ is hydrogen or $C_1$-$C_4$ alkoxy; and T is $C_1$-$C_4$ alkyl, a halogen, a hydroxy group, $O(C_1$-$C_4)$ alkyl, or —$CH_2B$, wherein B is a nucleophile residue; and where the compound is administered in an amount therapeutically effective to treat the sexual dysfunction or enhance the sexual function of said mammal.

23. The method of claim 22 wherein the compound is without clinically significant antibacterial activity.

24. The method of claim 22 wherein the amount is less than an antiobiotically effective amount.

25. The method of claim 22 wherein the mammal is male.

26. The method of claim 25 wherein the sexual dysfunction is erectile dysfunction.

27. The method of claim 25 wherein the sexual dysfunction is premature ejaculation.

28. The method of claim 22 wherein the mammal is female.

29. The method of claim 28 wherein the enhanced sexual function is increased libido.

* * * * *